(12) United States Patent
Chung et al.

(10) Patent No.: US 8,030,244 B2
(45) Date of Patent: Oct. 4, 2011

(54) METHOD, COMPOSITION AND KIT FOR PROMOTIONG PLANT GROWTH AND IMPROVING PLANT PRESERVATION

(75) Inventors: Guk Hoon Chung, Seongnam-si (KR); Ji Heun Hong, Yongin-si (KR); Young Lae Yang, Yongin-si (KR)

(73) Assignee: Doosan Corporation, Seoul (KR)

( * ) Notice: Subject to any disclaimer, the term of this patent is extended or adjusted under 35 U.S.C. 154(b) by 880 days.

(21) Appl. No.: 11/910,390

(22) PCT Filed: Apr. 3, 2006

(86) PCT No.: PCT/KR2006/001224
§ 371 (c)(1),
(2), (4) Date: Jan. 9, 2008

(87) PCT Pub. No.: WO2006/104372
PCT Pub. Date: Oct. 5, 2006

(65) Prior Publication Data
US 2010/0255990 A1    Oct. 7, 2010

(30) Foreign Application Priority Data
Apr. 1, 2005  (KR) .................. 10-2005-0027739

(51) Int. Cl.
*A01N 59/00* (2006.01)
(52) U.S. Cl. ...................... 504/123; 424/722
(58) Field of Classification Search .............. None
See application file for complete search history.

(56) References Cited

U.S. PATENT DOCUMENTS

| | | | |
|---|---|---|---|
| 5,110,341 A | 5/1992 | Palta et al. | |
| 5,126,155 A | 6/1992 | Palta et al. | |
| 6,284,709 B1 | 9/2001 | Ju et al. | |
| 6,284,719 B1 | 9/2001 | Simms | |
| 6,559,099 B1 * | 5/2003 | Farag et al. | 504/194 |

FOREIGN PATENT DOCUMENTS

| | | | |
|---|---|---|---|
| HU | 2901 H | * | 1/1984 |
| JP | 10095703 | * | 4/1998 |
| KR | 1020030028080 | | 4/2003 |

OTHER PUBLICATIONS

Sheen, J., "Metabolic repression of transcription in higher plants," *The Plant Cell* (1990) 2: 1027-1038.
Farag et al., "Stimulation of ethylene production by urea, thidiazuron,, and lysophosphatidlethanolamine and possible sites of this stimulation ." *Annual Meeting of the American Society of Plant Physiologists* (1989): 95.
Wang et al., "Foliar application of potassium silicate induces metabolic changes in strawberry plants." *Journal of Plant Nutrition* 21;1(1998): 157-167.
Palta et al., "Inhibition of phospholipase D by lysophosphatidylethanolamine, a lipid-derived senescence retardant." *Proceedings of the National Academy of Sciences of the United States of America* 94(1997): 12717-12721. Review Based on search report of Jan. 9, 2008.
Kaur et al., "Postharvest dip in a natural lipid, lysophosphatidylethanolamine, may prolong vase life of Snapdragon flowers." *Hortscience* 32;5(1997): 888-890.
Epstein, "Silicon." *Annu. Rev. Plant Physiol. Plant Mol. Biol.* 50(1999): 641-664.

* cited by examiner

*Primary Examiner* — Alton Pryor
(74) *Attorney, Agent, or Firm* — Merchant & Gould P.C.

(57) ABSTRACT

Disclosed are a method, composition and kit for promoting plant growth and improving plant preservation. According to the invention, it is possible to improve qualities of agricultural products and preservation of crops after harvested as well as to increase production of crops by promoting plant growth without using toxic chemicals.

6 Claims, 11 Drawing Sheets

METHOD, COMPOSITION AND KIT FOR PROMOTIONG PLANT GROWTH AND IMPROVING PLANT PRESERVATION

TECHNICAL FIELD

The present invention relates to a method, composition and kit for promoting plant growth and improving plant preservation. More specifically, the invention relates to a method, composition and kit capable of promoting ripening of a plant, particularly a fruit useful for human to advance the harvest time of the fruit and improving the preservation of the harvested fruit to preserve a value of the product for a long time.

BACKGROUND ART

In producing crops, many chemicals are used so as to promote plant growth and to improve a quality of the crops. A lot of chemicals are abused, such as chemicals for promoting the seed germination, plant growth or fruit ripening, chemicals for protecting the plant against various pathogens and chemicals for improving the preservation and storage of the crops harvested.

In order to solve the above problem, a variety of organic cultivation methods are recently developed. As the interest in the health is tremendously increased, the vegetables organically grown are spotlighted. However, it is difficult to produce the crops, which are quantitatively and qualitatively excellent, only with the existing organic cultivation methods.

It has been known that lysophosphatidylethanolamine plays a very important role in the ripening and senescence of the fruit. It has been known that the senescence of the leaves and the fruits of tomato are suppressed with the treatment of lysophosphatidylethanolamine. It has been also known that the preservation time of the fruit of tomato can be prolonged with the treatment of lysophosphatidylethanolamine after the harvest (see U.S. Pat. Nos. 5,110,341 and 5,126,155). In addition, it has been known that if an apple is treated with the lysophosphatidylethanolamine, the formation of anthocyanin in the skin thereof is promoted and the loss of firmness during the preservation period of the apple harvested is suppressed. It is known that these effects are related to functions of lowering a respiration rate of fruits such as an apple, cranberry, tomato and the like and promoting or suppressing the formation of ethylene gas (Farag, K. M. and J. P. Palta, 'Stimulation of Ethylene Production by Erea, Thidiazoron, and Lysophosphatidylethanolamine and Possible Sites of This Stimulation' Annual Meeting of the American Society of Plant Physiologists, April 1989).

The lysophosphatidylethanolamine solution having a concentration properly adjusted is often used as the means for prolonging a lifetime of the cut flower (HortScience 32(5): 888-890, 1997).

In the mean time, the silicone, which exists in the plant, is known to change the metabolism of the plant. Specifically, if the plant is treated with the silicone, an amount of chlorophyll is increased and the plant growth is promoted. In addition, it is supposed that the silicone protects the plant against the damage from disease and harmful insects and helps the normal growth, occurrence, survival and reproduction (S. Y. Wang, et al., Journal of plant nutrition, 21(1), 157-167 (1998); Emanuel Epstein, Annu. Rev. Plant Physiol. Plant Mol. Biol. 50:641-64 (1999)).

In addition, in order to promote the plant growth and to improve the preservation thereof, it has been suggested a composition including potassium silicate, sodium silicate, potassium carbonate, sodium carbonate, sodium bicarbonate, etc. and a method for manufacturing the same (see U.S. Pat. No. 6,284,709). It is disclosed that if the plant is treated with a composition including potassium silicate, sodium silicate, potassium carbonate, sodium carbonate, potassium chloride and reducing sugar, the plant growth is promoted, the propagation of microorganism is suppressed, the physical properties are improved and the preservation of the agricultural products is prolonged.

However, it is impossible to effectively promote the plant growth only with the above methods and the preservation property is not attained in a satisfactory level. Accordingly, it is needed an alternative capable of harvesting the fruit of high quality in a large amount and preserving the harvested fruit for a longer time while less using the chemicals harmful for the body and the environments.

DISCLOSURE

Technical Problem

Accordingly, the present invention has been made to solve the above problems. An object of the invention is to provide method, composition and kit capable of promoting the plant growth, increasing the preservation property of the crops after the harvest and the quality of the agricultural products, without using the toxic chemicals.

Technical Solution

In order to achieve the above objects, there is provided a method for promoting plant growth and improving plant preservation stability comprising treating a plant with lysophosphatidylethanolamine and silicate.

In the above method, the silicate may be at least one of sodium silicate and potassium silicate.

In the above method, a weight ratio of lysophosphatidylethanolamine:silicate is preferably 1:0.1 to 1:50, more preferably 1:0.5 to 1:10, most preferably 1:1 to 1:2.

There is provided a composition for promoting plant growth and improving plant preservation stability containing lysophosphatidylethanolamine and silicate as effective ingredients.

In the above composition, the silicate may be at least one of sodium silicate and potassium silicate.

In the above composition, a weight ratio of lysophosphatidylethanolamine:silicate is preferably 1:0.1 to 1:50, more preferably 1:0.5 to 1:10, most preferably 1:1 to 1:2.

In the above composition, the lysophosphatidylethanolamine and the silicate exist under non-contact state from each other in the composition.

There is provided a kit for promoting plant growth and improving plant preservation stability comprising a first solution containing lysophosphatidylethanolamine and a second solution containing silicate.

In the above kit, the silicate may be at least one of sodium silicate and potassium silicate.

The above kit may further comprise a first space for putting the first solution therein and a second space for putting the second solution therein.

In the above kit, a weight ratio of lysophosphatidylethanolamine contained in the first solution and the silicate contained in the second solution is preferably 1:0.1 to 1:50, more preferably 1:0.5 to 1:10, most preferably 1:1 to 1:2.

Advantageous Effects

The present invention can promote the plant growth to increase production of the crops, improve the preservation of the crops after harvest, and improve a quality of the crops, without using toxic chemicals.

DESCRIPTION OF DRAWINGS

FIGS. 7a to 7c are photographs showing a color change of the grape fruit when the combination of the LPE and the silicate is treated.

FIGS. 8a to 8c are photographs showing a color change of the leaves of a grapevine.

BEST MODE

Hereinafter, it is specifically described the method, composition and kit of the invention.

Herein, the term "plant" includes any part, tissue and organ originating from an alive plant as well as the alive plant. For example, the "plant" includes a fruit, a flower, a tuber, a root, a stem, a leaf, a seed and the like.

The "lysophosphatidylethanolamine (LPE)" used in the specification is one of the lysophosphatides, naturally exists in the cells of animals and plants. In particular, it is much included in the yolk and the brain cell. The LPE can be induced from the phosphatidylethanolamine which is one of the phosphatides found in the cell membrane. The LPE derived from animals and plants or microbes, induced from phosphatidylethanolamine or synthesized chemically may be used.

The "silicate" used in the specification is meant by a silicate and is a broad conception including sodium silicate, potassium silicate, magnesium silicate, aluminum silicate, potassium aluminum silicate, meta silicate, sodium poly silicate, ethyl silicate, methyl silicate, tri calcium silicate, borosilicate, barium silicate, cupper silicate and the like. Among them, the sodium silicate and the potassium silicate are particularly preferable.

The "promotion of plant growth" used in the specification is the most comprehensive concept including the germination promotion of a plant seed, the promotion of a length growth and a volume growth of a plant, the promotion of a fruit set of a fruit, the promotion of a ripening of a fruit, the improvement of a leaf activation, the promotion of a root growth, the promotion of a coloration of a fruit and the like.

When the lysophosphatidylethanolamine, the sodium silicate or potassium silicate exist and contact each other in one water-soluble composition, the ester bond of the LPE is hydrolyzed due to the high pH of the sodium silicate or potassium silicate. This problem can be solved by adopting one of the conventional known methods. For example, the LPE and the silicate may exist in the composition under the state that they are captured in a capsule not to contact each other, and then the materials in the capsule may be discharged by applying a physical or chemical change when using it.

In the kit of the invention, it is preferred that the LPE and the silicate are separately stored. For example, in a vessel having a wall therein, the LPE and the silicate are separately kept in the vessel by the wall. Alternatively, they may be kept in each of two vessels included in the kit. Then, when using it, they may be mixed. In order to satisfy the weight ratio suggested by the invention, a spray injector may pull up and mix the LPE and the silicate having different concentrations in a same volume, which are separately kept, and may be operated to spray the LPE and the silicate with mixed.

The invention relates to a synergy effect of the lysophosphatidylethanolamine and the silicate for promoting the plant growth and improving the preservation stability of the crops. Although it is impossible to know a specific mechanism causing the synergy effect, the inventors suppose that the silicate increases the dispersion property of the LPE, improves a solubility of the LPE, and helps the LPE to adhere to the plant, thereby maximizing the effect of the LPE.

In order to achieve the effect of the invention, a weight ratio of the LPE and the silicate is preferably 1:0.1 to 1:50. If an amount of the silicate to the LPE is too small, an efficacy of the silicate is little, so that the object of the invention cannot be achieved. If an amount of the silicate is too great, it reduces the effect of the LPE. From this viewpoint, it is more preferably 1:0.5 to 1:10, most preferably 1:1 to 1:2.

MODE FOR INVENTION

Hereinafter, the invention will be more specifically described with reference to the examples. The examples are provided to illustrate the invention, not to limit it.

Example 1

The inventors carried out the following experiments so as to prove a synergy effect of a combination of lysophosphatidylethanolamine and silicate.

The grape was selected as a test plant. Crimson and red globe (scientific name: *Vitis Vinifera* sp.) were used as the grape. The materials used in the respective treatments are shown in following table 1.

TABLE 1

| classification | composition |
| --- | --- |
| Experimental group 1 | solution of LPE 10% + solution of potassium silicate |
| Control group 1 | Non-treatment (buffer treatment group) |
| Control group 2 | Ethrel ™ (Bayer CropScience company) |
| Control group 3 | solution of LPE 10% |
| Control group 4 | solution of potassium silicate |
| Control group 5 | Non-treatment |

The solution of LPE 10% a solution wherein the LPE is dissolved in a concentration of 10% in a mixed solution of water, isopropanol, butanol, hexanol and oleyl alcohol.

The experimental group 1 is the case wherein they are treated with the solution of potassium silicate (wherein the silicate content is 100 ppm) and the LPE solution (wherein the LPE content is 50 ppm) with an amount of 200 GPA thereof.

The control group 1 is a non-treatment group which is set as a buffer between each experimental group and control group and represents another negative control group. The buffer exists to secure a certainty of whether or not the treatment and is meant by a non-treated row which is between the rows treated with chemicals, among the cultivation rows.

The control group 2 is the case where they are treated with Ethrel, which is widely sold and used as a plant growth regulator, in an amount of 400 ppm, 100 GPA.

The control group 3 is such that it is treated with the solution of LPE 10% in an amount of 50 ppm, 200 GPA.

The control group 4 is such that it is treated with the solution of potassium silicate in an amount of 100 ppm, 200 GPA.

The control group 5 is a negative control group which is not treated.

The solutions were injected in a spray manner, except the control groups 1 and 5. The each treatment was carried out for an area of 5 acres. All treatments were carried out with a typical orchard air blast sprayer.

All harvests after the each treatment were carried out by the workers belonging to the farm according to the ordinary harvesting method, so that the grapes were harvested in accordance with a commercial standard. The number and grade of the box harvested from the respective treatment row were recorded for each harvest day, with regard to the each treatment.

1. First Experiment—Continuous Application to the Crimson

For the crimson which is cultivated in California, the above 6 treatments were successively carried out two times. The secondary treatment was carried out at the time when the 40 days have elapsed after the first treatment.

Figure 1:
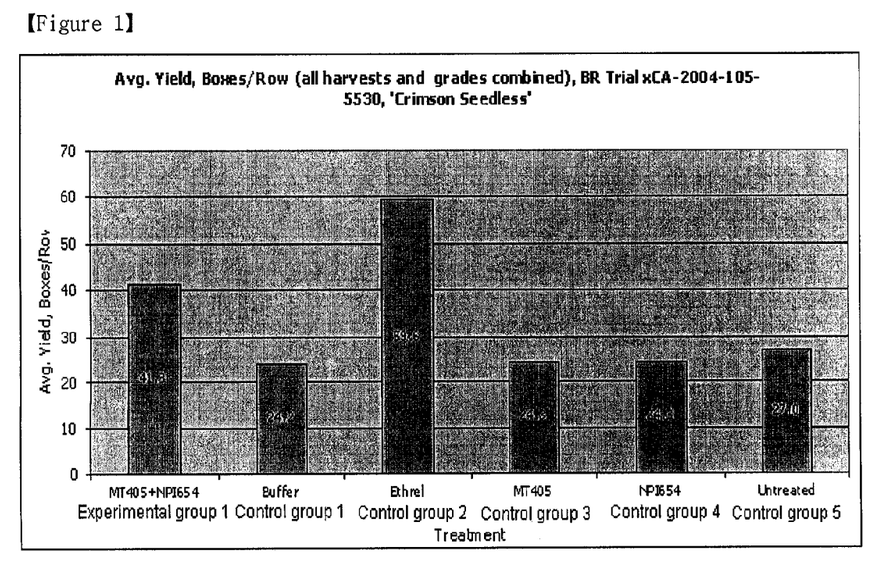
FIG. 1 is a graph showing a result obtained by consecutively carrying out each treatment two times for crimson, with a yield of the crimson.

As a result, the yields of the grapes for each of the experimental group and the control groups harvested were shown in FIG. 1. As shown in FIG. 1, the yield of the control group 2 (Ethrel) was the highest and the yield of the experimental group 1 (LPE+Si) was next. The yields of the control group 3 (LPE) and the control group 4 (Si) were smaller than those of the control groups 1 and 5 which were not treated.

In case of the sole treatment of the LPE or Si, the yields thereof were smaller than the case where no treatment was carried out. However, when the LPE and Si were combined and treated, the yields were considerably increased. This proves the synergy effect of the LPE and the Si.

2. Second Experiment—Single Application to the Crimson

For the crimson which is cultivated in California, the above 6 treatments were carried out. The treatment was carried out only one time.

Figure 2:
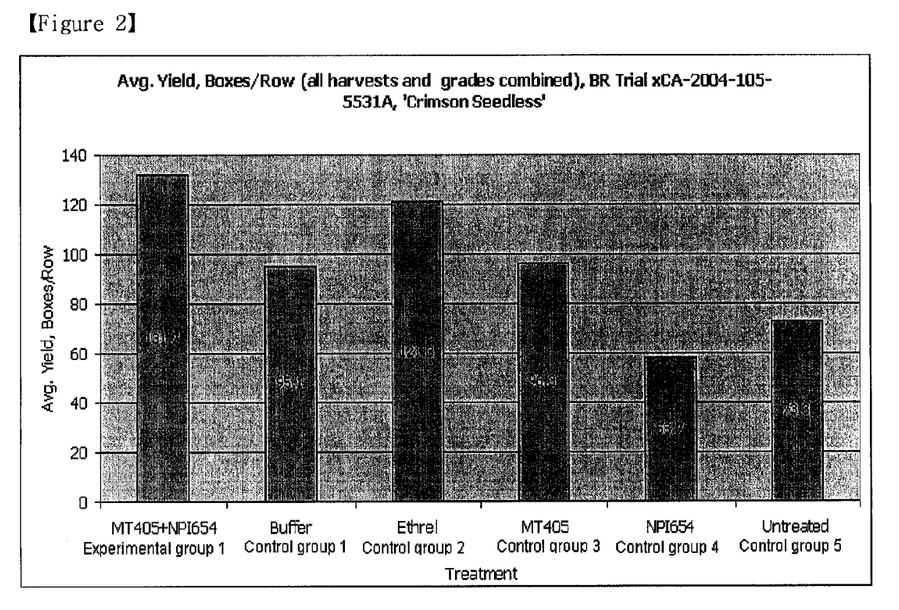
FIG. 2 is a graph showing a result obtained by carrying out each treatment one time for crimson, with a yield of the crimson.

A result thereof is shown in FIG. 2. As shown in FIG. 2, the yield of the experimental group 1 (LPE+Si) was the highest and the yield of the control group 2 (Ethrel) was next. The yield of the control group 4 (Si) was smaller than those of the control groups 1 and 5 which were not treated. Although the control group 3 (LPE) showed a yield of 96.3 and the control group 4 (Si) showed a yield smaller than that of the non-treatment group, the experimental group 1 which was treated with LPE and Si showed an increased yield of 131.7. This proves a synergy effect resulting from a combination use of the LPE and the Si.

3. Third Experiment—Continuous Application to the Red Globe

For the red globe which is cultivated in California, the above 6 treatments were successively carried out two times. The secondary treatment was carried out at the time when the 40 days have elapsed after the first treatment.

Figure 3:
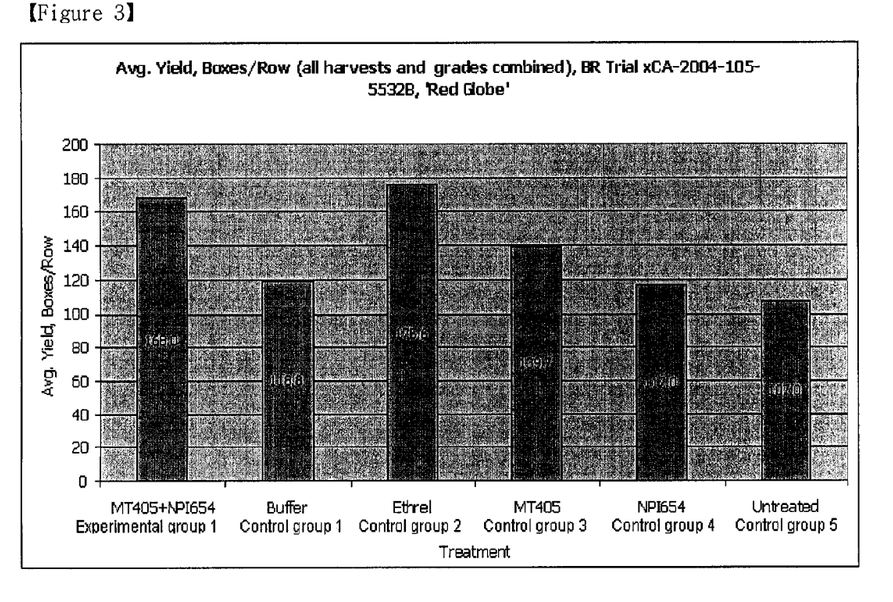
FIG. 3 is a graph showing a result obtained by consecutively carrying out each treatment two times for red globe, with a yield of the red globe.

A result thereof is shown in FIG. 3. As shown in FIG. 3, the yield of the control group 2 (Ethrel) was the highest and the yield of the experimental group 1 (LPE+Si) was next. It should be paid attention to that although the control group 3, which was treated with the LPE only, showed an increase of about 22 boxes and the control group 4, which was treated with Si only, showed an increase of 10 boxes, as compared to the control groups 1 and 5, which were not treated, the experimental group 1, which was treated with a combination of the LPE and Si, showed an increase of 60 boxes or more. This proves the synergy effect resulting from the combination use of the LPE and the Si.

Example 2

In order to prove the synergy effect resulting from the combination of LPE and Si more clearly, the inventors used a method for measuring reactive oxygen species (ROS).

1. Plant Materials and Growth Condition

The corns (Zea mays L) were used according to the following procedures: seeds of Golden cross Bantam were sufficiently washed in the flowing water and immersed in the distilled water for 24 hours. Then, the seeds were arranged in a line on the cultivation dish where the paper wetted with the distilled water was put on the cultivation dish and the ventral side of the seeds was forced to touch with the dish bottom. The seeds were covered with the wetted paper by two folds. They were subject to the germination process in a darkroom for 48 hours in which the humidity and the temperature were maintained to be 60% and 28±1° C., respectively. The individuals having the root length of 1.5~2 cm were selected and used in this experiment.

2. Preparation of Protoplast of Corn Root

The protoplast of the corn root etiolated was modified according to the following method (Sheen J, Metabolic repression of transcription in higher plants, Plant Cell, 1990 October: 2(10):1027-38).

In other words, the protoplast was separated from the two-day etiolated young corn plant. The root was subject to the decomposition process in an enzyme solution containing the following ingredients at 22° C. for 5 hours: 2% (w/v) cellulase 'Onozuka' RS (Yakult Pharmaceutical Company Ltd.), 2% (w/v) Cellulysin (Calbiochem, Behring Diagnostic, La Jolla, USA), 0.026% (w/v) pectolaiase Y23 (Sigma, St. Louis, USA), 0.6M mannitol, 10 mM Mes (pH 5.7), 1 mM $CaCl_2$, 1 mM $MgCl_2$, 10 Mm β-mercaptoethanol and 0.1% (w/v) calf albumin (Sigma, St. Louis, USA). The protoplasts were separated from the tissues which were partially decomposed through the mesh. The protoplast was washed with a solution containing 0.45M mannitol and 1 mM $CaCl_2$ for three times, stored under dark condition and used for the experiment.

3. Liquid Medicine Treatment

For the protoplasts prepared in the above 2, the LPE 20 ppm solely (control group 6), the LPE 40 ppm solely (control group 7), the sodium silicate 50 ppm solely (control group 8), the sodium silicate 100 ppm solely (control group 9), the LPE 20 ppm+sodium silicate 50 ppm (experimental group 2), and the LPE 50 ppm+sodium silicate 100 ppm (experimental group 3) were respectively incubated for 5 minutes.

4. Flow Cytometry

After the incubation, the cells were reacted in a dark place with 5 μM 2',7'-dichlorofluorescine diacetate (DCF-DA) (Molecular Probes, USA) for 5-10 minutes. The compound was converted into 2',7'-dichlorofluorescein (DCFH) by the esterase in the cell, which was in turn oxidized by the reactive oxygen species such as $H_2O_2$ and thus changed into 2',7'-dichlorofluorescine (DCF) having the highest fluorescence. The fluorescence intensity was measured with FACScan (Beckton Dickinson, Bedford, USA) having excitation and emission settings of 488 nm and 530 nm, respectively. The count of cells was stopped at 30,000. In order to remove the apoptotic cell and debris before collecting the data, the gating was carried out. The results are shown in FIGS. 4 to 6.

Figure 4:
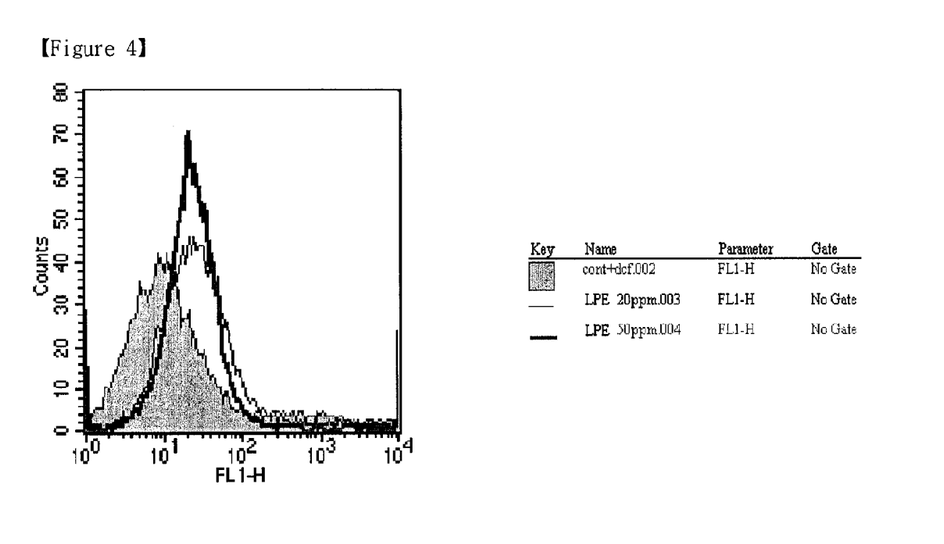
FIG. 4 is a graph of ROS in a case where 10% LPE is solely treated with concentrations of 20 ppm and 50 ppm.

FIG. 4 is a graph in a case where 10% LPE is solely treated with concentrations of 40 ppm and 100 ppm, respectively. As shown in FIG. 4, the amount of ROS was increased in both cases of 20 ppm and 50 ppm, and the increase amount was 200~300%. In the graphs of FIGS. 4 to 6, the increase of ROS amount is shown in a x-axis of a log scale, rather than a y-axis of a count degree, and is represented by how extent a peak in the graph is shifted to the left or right.

Figure 5:
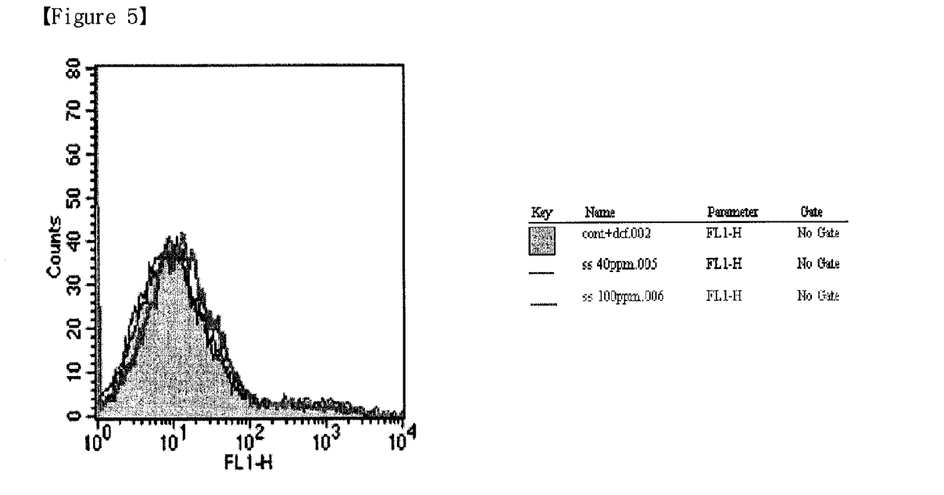
FIG. 5 is a graph of ROS in a case where sodium silicate is solely treated with concentrations of 40 ppm and 100 ppm.

FIG. 5 is a graph in a case where sodium silicate is solely treated with concentrations of 40 ppm and 100 ppm. As shown in FIG. 5, there is little difference between the two concentrations.

Figure 6:
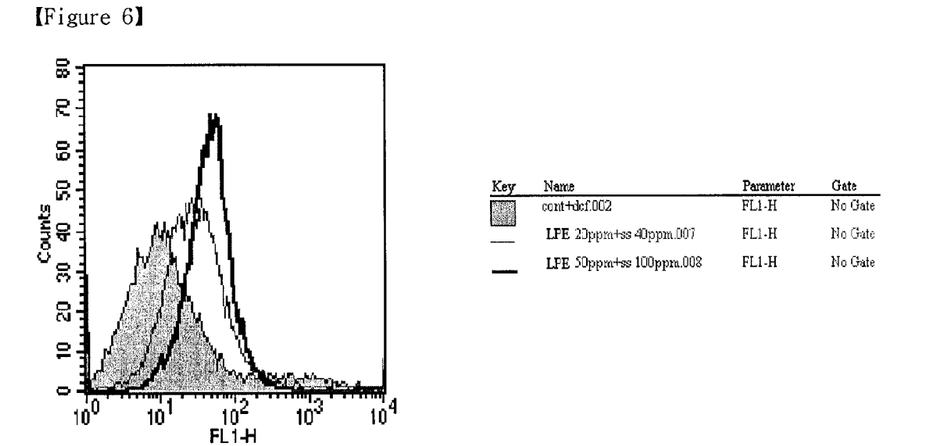
FIG. 6 is a graph of ROS in cases where a combination of the 10% LPE 20 ppm and the sodium silicate 40 ppm is treated and a combination of the 10% LPE 50 ppm and the sodium silicate 100 ppm is treated.

FIG. 6 is a graph in cases where a combination of the LPE 20 ppm and the sodium silicate 40 ppm is treated and a combination of the LPE 50 ppm and the sodium silicate 100 ppm is treated. In the case where a combination of the LPE 20 ppm and the sodium silicate 40 ppm is treated, the increase amount was 200~300%. In the case where a combination of the LPE 50 ppm and the sodium silicate 100 ppm is treated, the increase amount was 200~600%.

Summarizing the above results, when the LPE and sodium silicate were treated together, the ROS was considerably increased. The increase of ROS is meant by that the plant is stimulated and thus the bio mechanism is activated, thereby promoting the ripening and growth. Accordingly, it is proven through the results that when the LPE and the silicate are combined and used, it is obtained a synergy effect of promoting the plant growth.

Example 3

The inventors carried out a following experiment in order to check an effect of LPE and sodium silicate on coloring development in grapes.

Grapes used in the experiment were Muscat Bailey A (late-season cv.). Observation was done for the objects two weeks after conducting each of such treatments as shown in table 2, and the objects harvested in six days later therefrom.

TABLE 2

| Classification | Treatment |
| --- | --- |
| control group 10 | Non-Treatment |
| control group 11 | LPE 10% solution (50 ppm) 200 GPA |
| experimental group 4 | LPE 10% solution (50 ppm) + sodium silicate solution (100 ppm) 200 GPA |

Figure 7A:
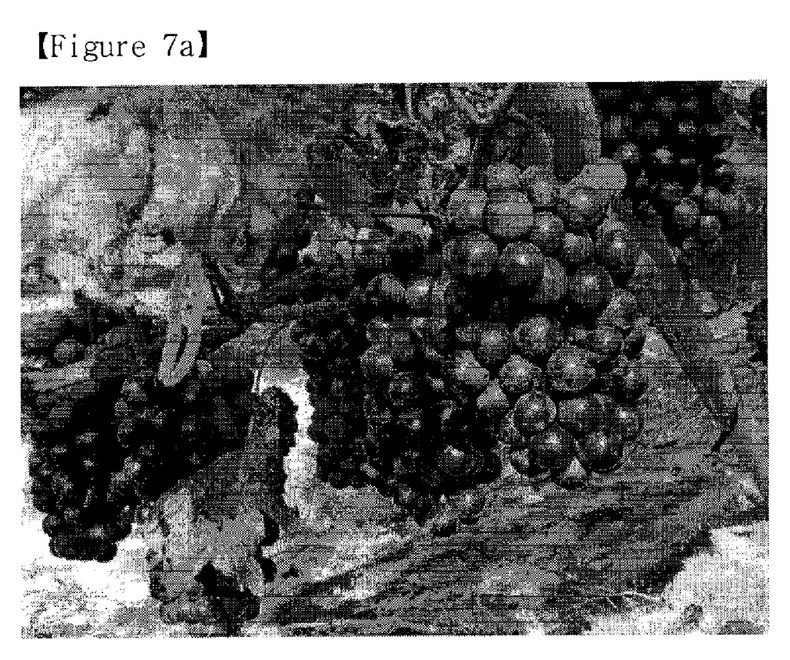
FIG. 7a is a result of a non-treated group.
Figure 7B:
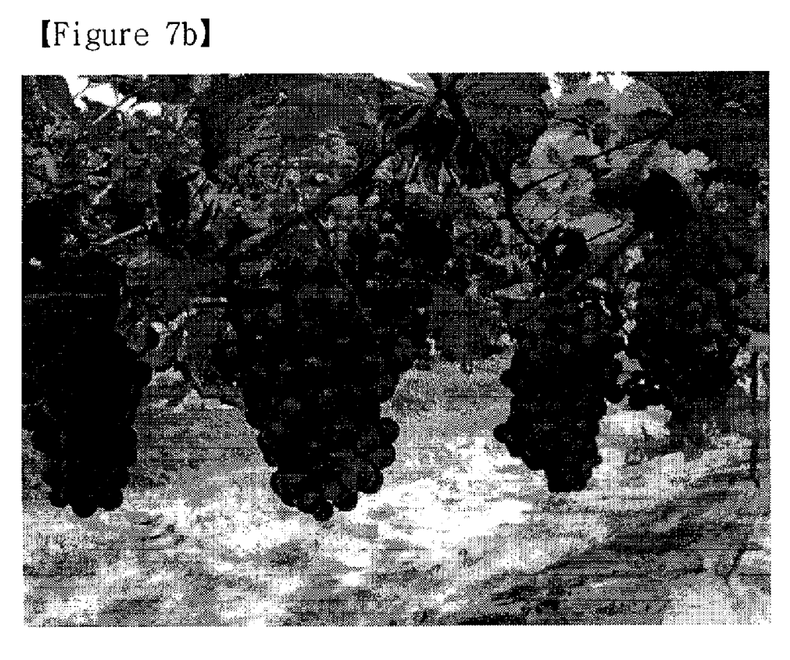
FIG. 7b is a result of a LPE 50 ppm treatment (control group 11)
Figure 7C:
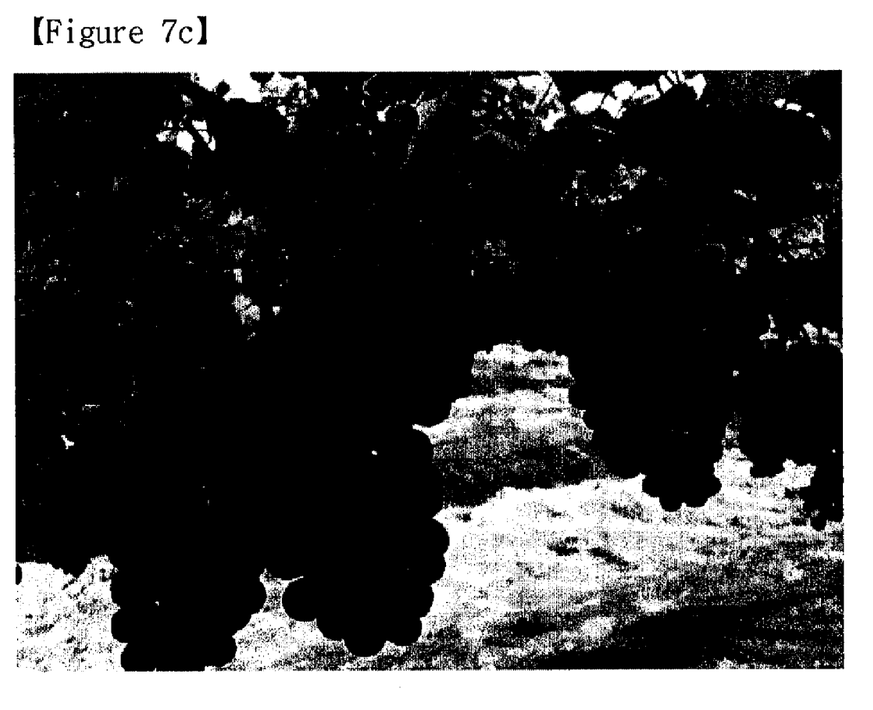
FIG. 7c is a result of a treatment (experimental group 4) of LPE 50 ppm+sodium silicate 100 ppm.
Figure 8A:
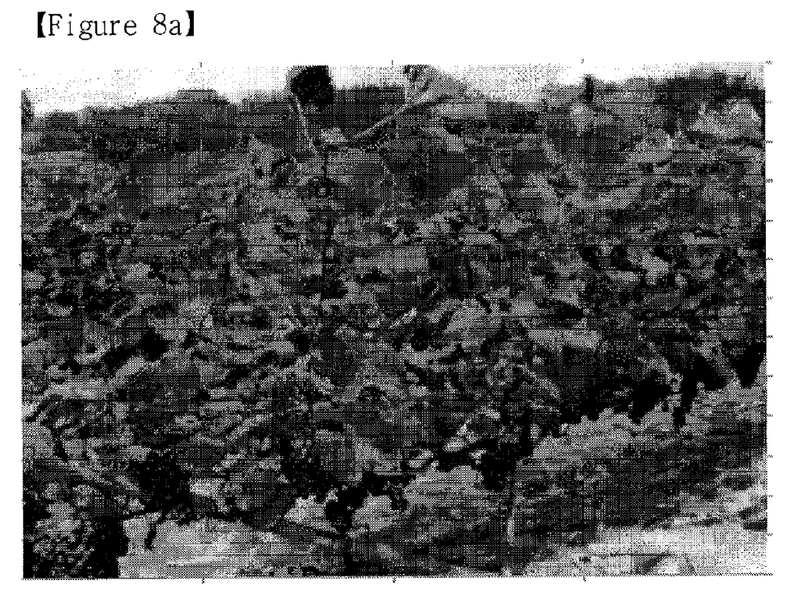
FIG. 8a is a result of a non-treated group of a control group 10.
Figure 8B:
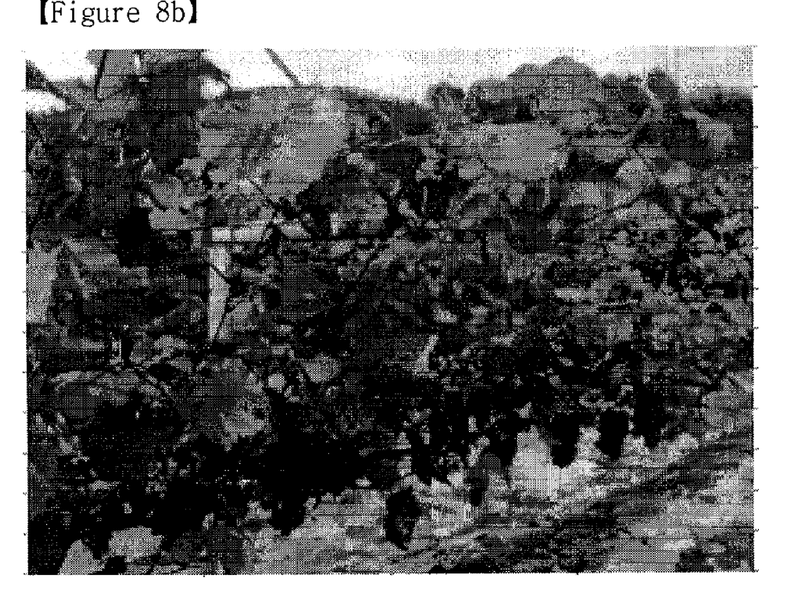
FIG. 8b is a result of a LPE 50 ppm treatment (control group 11) and FIG. 8c is a result of a treatment (experimental group 4) of LPE 50 ppm+sodium silicate 100 ppm.
Figure 8C:
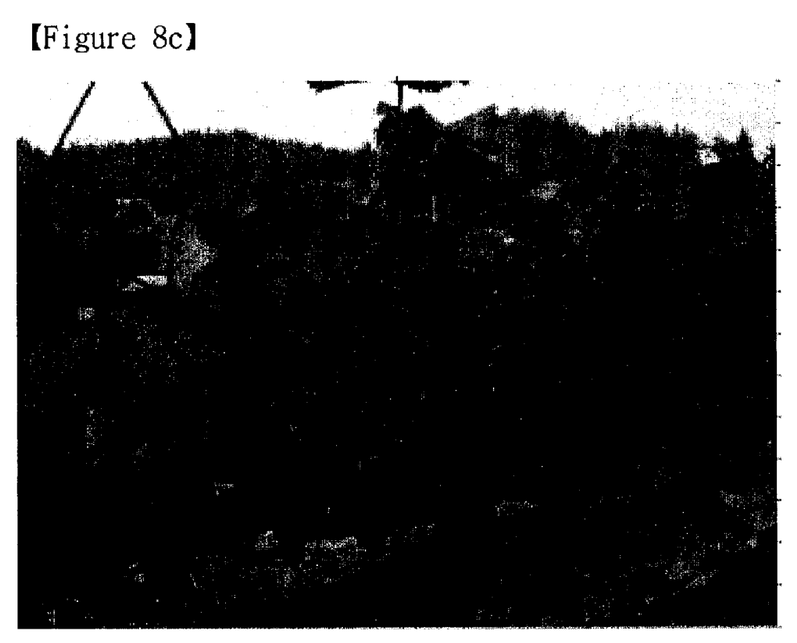

A result of the observation after two weeks has been shown in FIGS. 7a to 7c regarding the colors of grape fruit and in FIGS. 8a to 8c regarding those of grape leaves.

FIGS. 7a to 7c are photographs showing results of the control group 10 with no treatment, the control group 11 treated with LPE 50 ppm, and the experimental group 4 treated with a combination of LPE 50 ppm+sodium silicate 100 ppm, respectively.

As shown in FIGS. 7a to 7c, it has been indicated that the colors of grapes were excellent in the order of the experimental group 4, the control group 11, and the control group 10. Therefore, it can be seen that a promoting effect of LPE on the fruit coloring is furthermore improved by silicate.

Meanwhile, an observation after two weeks was also carried out for colors of grape leaves. Results thereof are shown in FIGS. 8a to 8c.

FIGS. 8a to 8c are photographs showing results of the control group 10 with no treatment, the control group 11 treated with LPE 50 ppm, and the experimental group 4 treated with a combination of LPE 50 ppm+sodium silicate 100 ppm, respectively.

As shown in FIGS. 8a to 8c, it can be seen that in case of the experimental group 4, almost all of leaves are maintained in green color, whereas in the cases of the control groups 10 and 11, many leaves become discolored to yellow. This proves that silicate has an effect to further improve a promoting effect of LPE on the activity of the leaves.

Example 4

Effect of a Combination of LPE and Silicate on an Adventitious Root Growth of Mung Beans The inventors carried out a biological test on the mung beans in order to examine an effect of the combination of LPE and silicate on the growth of the adventitious root of the mung beans.

The mung beans were cleaned with flowing water, immersed in the distilled water for 24 hours, transplanted in artificial culture soil, and finally grew under light for 10 days. When a length of hypocotyls became about 4 cm, mung beans grown in similar size were sorted and cut with their roots to an extent that the lengths of the hypocotyls reach 3.5 cm to 4 cm. The cut mung beans were classified into 8 groups, in which a first group was treated with no treatment (control; water), a second group was treated with sodium silicate 50 ppm (ss 50 ppm), a third group was treated with LPE 50 ppm (LPE 50 ppm), and a fourth group was treated with a combination of sodium silicate 50 ppm and LPE 50 ppm (ss 50 ppm+LPE 50 ppm). The experiment was carried out under light in the condition that the respective solutions were filled in test tubes of about 10 ml, the mung beans were provided to the test tubes one by one in such a manner that the hypocotyls are immersed deeply in the solutions, respectively.

In order to improve reliability of the experiment, the other four groups were treated with the same treatment as the above, and the experiment was carried out for the two sets of four groups at the same time.

Figure 9:
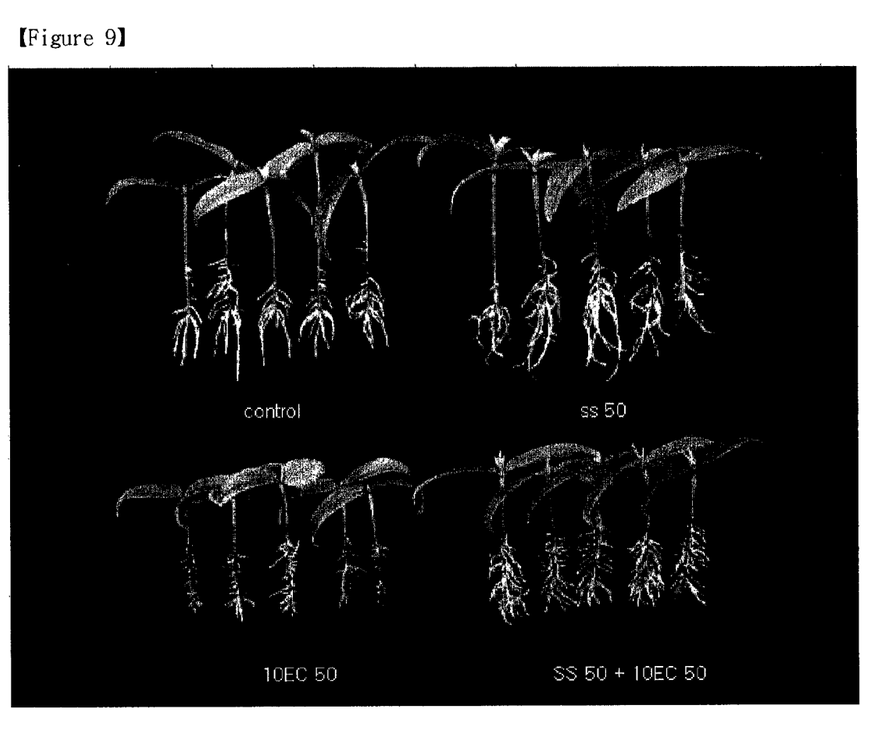
FIGS. 9 and 10 are photographs proving an effect of a combination treatment of LPE and silicate on the adventitious root growth of mung beans.
Figure 10:
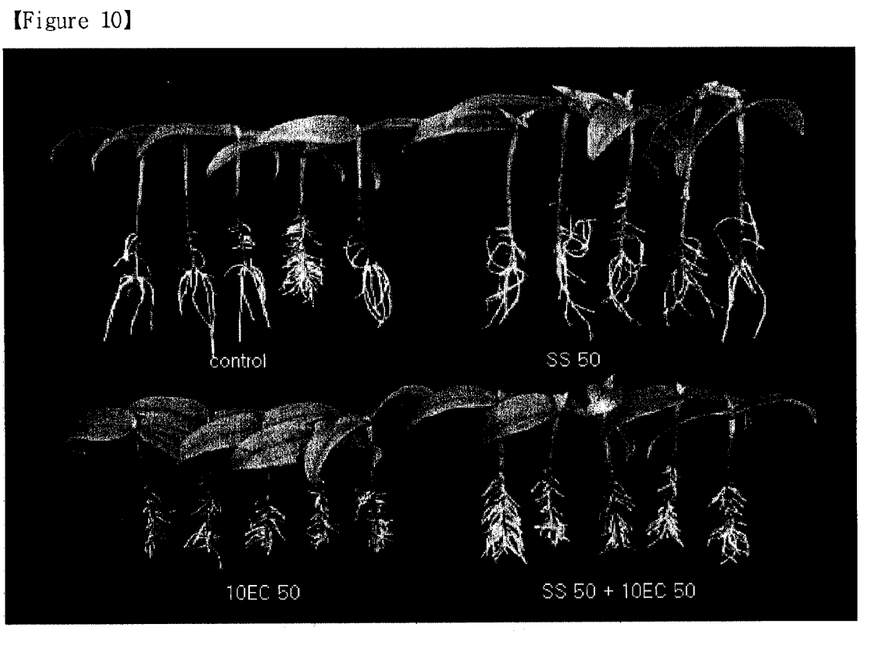

An observation was done for the state of the respective adventitious roots after two weeks after the respective treatment. The results thereof are shown in FIGS. 9 and 10. FIG. 9 is a result for the experiment of the first set, and FIG. 10 is a result for the experiment of the second set. As shown in FIGS. 9 and 10, it could be known that in case of "ss 50", the roots have a long length, but the number thereof is small, whereas in case of "LPE 50" the roots have a large number, but the length thereof is short. This proves that sodium silicate has an effect in promoting the growth of the adventitious roots in length, but has no effect in increasing the number of the roots, whereas LPE has an effect in increasing the number of the roots because it has the similar activity as auxin, but has no effect in lengthening the roots. However, in case of the combination treatment of sodium silicate and LPE (SS 50+LPE 50), it could be seen that the number of the roots is considerably large as compared to the case of the treatment using only sodium silicate, and that the length of the roots is considerably lengthened as compared to the treatment using only LPE. This proves that the combination of LPE and sodium silicate has a synergy effect on growth of the adventitious roots.

Example 5

Effect of the Combination Treatment of LPE and Silicate on the Preservation Stability of the Grape Fruit The grapes treated in the Example 3 were harvested, and preserved at a room temperature for 14 days. Then, calculation has been done for a ratio of complete grape fruits that were not decayed or no bruise. The result thereof is shown in following table 3.

TABLE 3

|  | Repeat 1 | Repeat 2 | Repeat 3 | Repeat 4 | Repeat 5 | Repeat 6 | Average |
|---|---|---|---|---|---|---|---|
| Control Group 10 (No Treatment) | 1.1 | 0 | 1.9 | 7.3 | 9.0 | 3.2 | 3.8 |
| Control Group 11 (LPE 10% Solution) | 14.2 | 15.6 | 4.0 | 0 | 3.7 | 3.7 | 6.9 |
| Experiment Group 4 (LPE 10% Solution + Sodium Silicate) | 62.5 | 35.0 | 25.6 | 35.2 | 34.7 | 17.5 | 35.1 |

As shown in table 3, it could be seen that the preservation stability is considerably improved in the case of the combination treatment of LPE and sodium silicate.

INDUSTRIAL APPLICABILITY

The present invention can promote the plant growth to increase production of the crops, improve the preservation of the crops after harvest, and improve a quality of the crops, without using toxic chemicals.

The invention claimed is:

1. A method for promoting plant growth and improving plant preservation stability comprising treating a plant with lysophosphatidylethanolamine and silicate, wherein the silicate is at least one of sodium silicate and potassium silicate and a weight ratio of the lysophosphatidylethanolamine and silicate is 1:1 to 1:50.

2. A composition for promoting plant growth and improving plant preservation stability containing lysophosphatidylethanolamine and silicate as effective ingredients, wherein the silicate is at least one of sodium silicate and potassium silicate and a weight ratio of the lysophosphatidylethanolamine and silicate is 1:1 to 1:50.

3. The composition according to claim 2, wherein the lysophosphatidylethanolamine and the silicate exist under non-contact state from each other in the composition.

4. The composition according to claim 2, wherein the lysophosphatidylethanolamine and the silicate exist under non-contact state from each other in the composition.

5. A kit for promoting plant growth and improving plant preservation stability comprising a first solution containing lysophosphatidylethanolamine and a second solution containing silicate, wherein the silicate is at least one of sodium silicate and potassium silicate and a weight ratio of the lysophosphatidylethanolamine and silicate is 1:1 to 1:50.

6. The kit according to claim 5, further comprising a first space for putting the first solution therein and a second space for putting the second solution therein.

* * * * *